United States Patent
Le Bras et al.

[11] Patent Number: 6,132,742
[45] Date of Patent: Oct. 17, 2000

[54] COSMETIC COMPOSITION IN THE FORM OF A SOFT PASTE

[75] Inventors: Véronique Le Bras, Paris; Dolorès Miguel, Bourg-la-Reine; François Pradier, Fontenay-aux-Roses, all of France

[73] Assignee: L'Oreal, Paris, France

[21] Appl. No.: 09/167,538

[22] Filed: Oct. 7, 1998

Related U.S. Application Data

[63] Continuation of application No. 08/783,747, Jan. 16, 1997, which is a continuation of application No. 08/378,388, Jan. 25, 1995.

[30] Foreign Application Priority Data

Jan. 25, 1994 [FR] France ................................. 94 00756

[51] Int. Cl.$^7$ .......................... A61K 6/00; A61K 7/021; A61K 7/025
[52] U.S. Cl. ............................ 424/401; 424/63; 424/64
[58] Field of Search ............................ 424/401, 63, 64, 424/DIG. 5

[56] References Cited

U.S. PATENT DOCUMENTS

| | | | |
|---|---|---|---|
| 3,911,105 | 10/1975 | Papantoniou et al. ................... | 424/64 |
| 5,053,220 | 10/1991 | Arraudeau et al. . | |
| 5,154,916 | 10/1992 | Arraudeau et al. ....................... | 424/64 |
| 5,234,682 | 8/1993 | Macchio et al. ........................ | 424/64 |
| 5,310,547 | 5/1994 | Dunphy et al. . | |
| 5,871,536 | 10/1998 | Arraudeau et al. . | |

FOREIGN PATENT DOCUMENTS

| | | |
|---|---|---|
| 0605284 | 7/1994 | European Pat. Off. . |
| 2232302 | 1/1975 | France . |
| 3243017 | 5/1984 | Germany . |
| 3744352 | 7/1989 | Germany . |
| 51-144740 | 12/1976 | Japan . |
| 59-7107 | 1/1984 | Japan . |
| 61-171412 | 8/1986 | Japan . |
| 61-236716 | 10/1986 | Japan . |
| 2-204405 | 8/1990 | Japan . |
| 2-243612 | 9/1990 | Japan . |
| 4-36211 | 2/1992 | Japan . |
| 5-220383 | 8/1993 | Japan . |
| 6-199630 | 7/1994 | Japan . |
| 7-196448 | 8/1995 | Japan . |
| 9116879 | 11/1991 | WIPO . |

Primary Examiner—Thurman K. Page
Assistant Examiner—Lakshmi Channavajjala
Attorney, Agent, or Firm—Nixon & Vanderhye P.C.

[57] ABSTRACT

The present invention relates to a cosmetic or dermopharmaceutical composition in the form of a soft paste, which can be used for making up or treating the skin or lips, comprising, in a fatty phase, from 12% to 60% by weight, relative to the total weight of the composition, of at least one wax having a melting point above 55° C., the said composition having a dynamic viscosity at 25° C. of between 3 and 30 pascal-seconds. The present invention also relates to the process for preparing this composition.

18 Claims, 1 Drawing Sheet

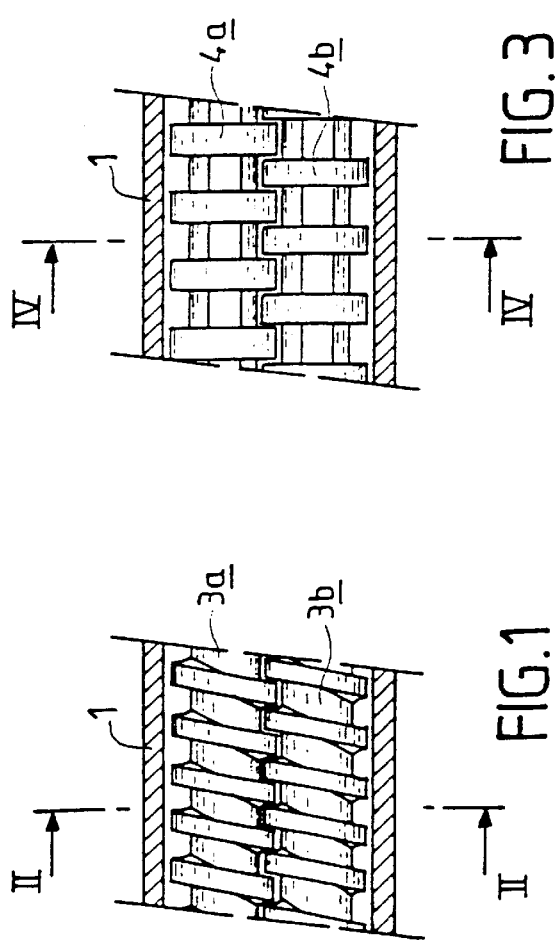

COSMETIC COMPOSITION IN THE FORM OF A SOFT PASTE

This is a continuation of application Ser. No. 08/783,747, filed Jan. 16, 1997, pending, which is a continuation of Ser. No. 08/378,388, filed Jan. 25, 1995.

The present invention relates to a composition in the form of a soft paste which can be taken up and applied for making up or treatment using an applicator such as a brush or a pen-style foam applicator, especially a lip rouge or lip treatment composition.

BACKGROUND OF THE INVENTION

Lip rouges can, in a known manner, take two forms: stick form and the form of a soft paste. The presentation in stick form, though widely used, has a number of drawbacks: it is difficult to impart a good outline to the lips using a stick, and the heat resistance of the stick is poor, which can cause it to soften and make it unusable.

Lip rouges in the form of a soft paste are taken up with an applicator, thereby overcoming the drawbacks of lipsticks. However, hitherto, by the traditional processes of manufacture, only a small amount of waxes can be introduced into cosmetic compositions in the form of soft pastes since, with increasing amounts of waxes, the viscosity of the pastes is increased, making them difficult to take up and apply; and when large amounts of waxes are incorporated, a solid is generally obtained which is usable only in stick form.

Now, waxes play an important part in the cosmetic qualities required of a cosmetic composition, in particular of a lip rouge, especially the qualities of consistency, creaminess, staying power of the applied film and thickness of the said film; the soft pastes obtained hitherto, for example according to Patents U.S. Pat. No. 5,085,855 and U.S. Pat. No. 4,935,228, do not generally contain waxes, or contain an amount of less than 12%, and they are consequently perceived by the user as being too oily, too shiny and lacking in staying power.

BRIEF DESCRIPTION OF THE DRAWINGS

FIG. 1 shows an elevated section of a sleeve used on the shaft of the mixer employed.

FIG. 2 shows a transverse section along II—II.

FIG. 3 shows an elevated section of a sleeve used on the shaft of the mixer employed.

FIG. 4 shows a transverse section along IV—IV.

FIG. 5 shows an elevated section of a sleeve used on the shaft of the mixer employed.

FIG. 6 shows a transverse section along VI—VI.

DETAILED DESCRIPTION OF THE INVENTION

The subject of the present invention is a cosmetic or dermopharmaceutical composition in the form of a soft paste, which can be used for making up or treating the skin or lips, containing at least one wax in a fatty phase, characterized in that it contains from 12% to 60% by weight, relative to the total weight of the composition, of at least one wax having a melting point above 55° C., and in that it has a dynamic viscosity at 25° C. of between 3 and 30 pascal seconds, measured with a CONTRAVES TV rotational viscometer equipped with an "MS-r4" moving element with a frequency of 60 Hz.

The composition according to the invention preferably contains 15 to 40% by weight of waxes having a melting point above 55° C.

The composition according to the present invention having a wax content of greater than 12% by weight is capable, on application in a layer, for example to the lips, of forming a film having good staying power. Furthermore, since its dynamic viscosity is less than 30 pascal seconds, it can be readily taken up and applied using an applicator.

The composition according to the present invention is hence a soft paste whose viscosity can be measured, as opposed to the solid structure of a stick whose viscosity cannot be measured.

The waxes having a melting point above 55° C. are preferably waxes having a melting point of between 55 and 110° C. and a needle penetration value at 25° C. of between 3 and 40 as measured according to French Standard NFT 004 or American Standard ASTM D5. According to these standards, the needle penetration value is the measurement of the depth, expressed in tenths of a millimetre, to which a standardized needle weighing 2.5 g placed in a needle holder weighing 47.5 g (equivalent in total to 50 g) penetrates when placed on the wax to be tested for 5 seconds. According to the invention, the wax can be an animal, vegetable, mineral or synthetic wax. Among animal waxes, beeswaxes may be mentioned in particular. Among vegetable waxes, carnauba, candelilla and ouricury waxes, cork fibre waxes, sugar-cane waxes and Japan waxes may be mentioned inter alia. Among mineral waxes, paraffin waxes, microcrystalline waxes, lignite waxes and ozokerites may be mentioned especially. Among synthetic waxes, polyethylene waxae and the waxes obtained by Fischer-Tropsch synthesis may be mentioned in particular. All these waxes are well known to a person skilled in the art. It should be noted that lanolin wax does not correspond to the definition of waxes given above.

The fatty phase of the composition can contain, in a known manner, apart from the abovementioned wax(es), at least one fatty constituent having a melting point below 55° C.; this fatty constituent can be an oil or a fat.

Among oils capable of being used mixed with the wax (es), special mentioned may be made of the following:

mineral oils such as paraffin oil, liquid petrolatum and mineral oils having a boiling point of between 310 and 410° C., oils of animal origin such as perhydrosqualene, arara oil, vegetable oils such as sweet almond oil, calophyllum oil, palm oil, avocado oil, jojoba oil, olive oil, castor oil and cereal-germ oils such as wheat-germ oil and sesame oil, silicone oils such as dimethylpolysiloxane, synthetic esters such as purcellin oil, butyl myristate, isopropyl myristate, cetyl myristate, isopropyl palmitate, butyl stearate, hexadecyl stearate, isopropyl stearate, octyl stearate, isocetyl stearate, decyl oleate, hexyl laurate, propylene glycol dicaprylate, diisopropyl adipate, organic alcohols such as oleyl alcohol, linoleyl alcohol, linolenyl alcohol, isostearyl alcohol, octyldodecanol, esters derived from lanolic acid, such as isopropyl lanolate, isocetyl lanolate, esters derived from oleic acid, such as isopropyl oleate and isocetyl oleate, acetylglycerides, octanoates and decanoates of alcohols and polyols, such as those of glycol or glycerol, ricinoleates of alcohols and polyols, such as cetyl ricinoleate.

Among fats capable of being used mixed with the wax (es), special mention may be made of the following:

hydrogenated oils which are solid at 25° C., such as hydrogenated castor oil, hydrogenated palm oil, hydrogenated tallow, hydrogenated coconut oil;

fatty esters which are solid at 25° C., such as propylene glycol myristate and myristyl myristate, cetyl alcohol;

mono-, di- or triglycerides and sucroglycerides;

lanolins.

The above fatty constituents can represent 10 to 90% by weight of the composition.

The composition can also contain, in a known manner, at least one pulverulent colouring agent and/or at least one pulverulent inorganic or organic filler.

As pulverulent colouring agents, the following may be mentioned:

carbon black (CI 77,266), chromium oxides (CI 77,288 and 77,289), black, yellow and red iron oxides (CI 77,499, 77,492, 77,491), ultramarines (alumino-silicate polysulphides), manganese pyrophosphate, ferric blue (CI 77,510), titanium dioxide (CI 77,891) and some metal powders such as those of silver or aluminium;

pearlescent agents, which are generally used mixed with coloured pigments, such as bismuth oxychloride, titanium-coated mica, guanine crystals;

certain organic dyes, which are generally used mixed with coloured pigments, such as carmine (CI 75,470) and organic lakes; these lakes, which are commonly employed to impart a make-up effect to the lips and skin, are calcium, barium, aluminium or zirconium salts of acid dyes such as halo-acid, azo and anthraquinone dyes: among these lakes, those known under the following names may be mentioned especially (CI represents the codification in the "Colour Index"): D and C Red 21 (CI 45,380), D and C Orange 5 (CI 45,370), D and C Red 27 (CI 45,410), D and C Orange 10 (CI 45,425), D and C Red 3 (CI 45,430), D and C Red 7 (CI 15,850:1), D and C Red 4 (CI 15,510), D and C Red 33 (CI 17,220), D and C Yellow 5 (CI 19,140), D and C Yellow 6 (CI 15,985), D and C Green 5 (CI 61,570), D and C Yellow 10 (CI 77,002), D and C Green 3 (CI 42,053), D and C Blue 1 (CI 42,090).

These colouring agents can represent from 0.5 to 20% by weight relative to the total weight of the composition.

The pulverulent fillers may advantageously be chosen from the group composed of:

talc, which is a hydrated magnesium silicate, used in the form of particles generally less than 40 μm in size, this filler possessing moisture-absorbing properties and being used most particularly on account of its creamy feel;

micas, which are aluminosilicates of miscellaneous compositions and take the form of scales from 2 to 200 μm, and preferably from 5 to 70 μm, in size, and from 0.1 to 5 μm, and preferably from 0.2 to 3 μm, in thickness, these generally transparent micas being of natural origin (for example muscovite, margarite, roscoelite, lepidolite, biotite) or synthetic origin;

kaolin, which is a hydrated aluminium silicate, which takes the form of particles having isotropic forms generally less than 30 μm in size, and which possesses good fat-absorbing properties;

zinc and titanium oxides, generally used in the form of particles not exceeding a few micrometres in size, these oxides having a creamy feel, good covering power and considerable opacity;

precipitated calcium carbonate which, in the form of particles less than 10 μm in size, has a creamy feel;

magnesium carbonate and magnesium hydrogen carbonate, which possess, in particular, perfume-binding properties;

silica, especially spherical silica and the silica powder marketed under the name "CAB-O-SIL TS 530" by the company "CABOT";

spherical titanium dioxide, especially that marketed under the tradename "SPHERITITAN";

the glass and ceramic beads marketed by the company "3 M" under the tradename "MACROLITE";

metal soaps derived from an organic carboxylic acid having from 8 to 22 carbon atoms, and preferably from 12 to 18 carbon atoms, for example zinc, magnesium or lithium stearate, zinc laurate, magnesium myristate, these soaps, generally in the form of particles less than 10 μm in size, having a creamy feel and facilitating the adhesion of the powder;

non-expanded powders of synthetic polymers such as polyethylene, polystyrene, polyesters (for example polyethylene isophthalate or terephthalate), polyamides (for example nylon or poly-β-alanine), acrylate copolymers (for example the microporous microspheres sold by the company "DOW CORNING" under the tradename "POLYTRAP"), silicone resins, polymethacrylic acids of polystyrene (crosslinked with divinylbenzene), of teflon, such as "FLUON", particles marketed by the company "MONTEFLUO", "HOSTAFLON Q", particles marketed by the company "HOECEST", these powders consisting of particles less than 50 μm in size possessing absorbant properties and enabling a velvety appearance to be imparted;

expanded powders such as hollow microspheres made of thermoplastic material, prepared by known processes, such as those described in U.S. Pat. No. 3,615,972 and EP-A-056,219, it being possible for these microspheres to be made from all non-toxic and non-irritant thermoplastic materials, for example from polymers or copolymers of ethylenic derivatives such as polyethylene, polystyrene, from vinyl chloride/acrylonitrile copolymer, from polyacrylonitrile, from polyamides, from polyesters, from urea/formaldehyde polymers or from vinylidene chloride copolymers (such as vinylidene chloride/acrylonitrile); and, in particular, the microspheres marketed under the tradename "EXPANCEL" by the company "KEMANORD PLAST", or under the tradename "MICROPEARL F 80 ED" by the company "MATSUMOTO", powders of natural organic materials such as maize, wheat or rice starches, crosslinked or otherwise.

These fillers can represent up to 40% by weight relative to the total weight of the composition.

The composition can also contain, in a known manner, additives chosen from the group composed of formulation adjuvants and/or cosmetic and/or dermopharmaceutical active agents which are fat-soluble.

As a formulation adjuvant, at least one antioxidant is used in particular. Among antioxidants, the propyl, octyl and dodecyl esters of gallic acid, butylated hydroxytoluene and butylated hydroxyanisole may be mentioned. The antioxidant generally represents, by weight, from 0 to 3%, and preferably from 0.05 to 0.5%, relative to the total weight of the composition. The formulation adjuvant can also be a perfume and/or a preservative such as methyl or propyl para-hydroxybenzoate.

The cosmetic and/or pharmaceutical active agents which may be introduced into the composition are lipophilic compounds. Among these, there may be mentioned, for example, vitamin derivatives such as tocopherol esters and vitamin A esters, essential fatty acids, sphingocerils and sunscreen agents which are fat-soluble, anti-inflammatories and oily extracts of plants.

The cosmetic and/or dermopharmaceutical active agent can represent 0.05 to 5%, and preferably 0.5 to 3%, by weight relative to the total weight of the composition.

The composition can also contain fat-soluble polymers. Among these, polyalkylenes (in particular polyethylenes and polybutenes) and polyacrylates may be mentioned. Among polyalkylenes, polybutene, in particular that sold by the company "AMOCO" under the tradename "UDOPOL", may be mentioned. They can represent up to 25% of the composition.

Hitherto, to prepare cosmetic or dermopharmaceutical compositions in the form of soft paste not containing waxes or containing a small proportion of wax(es), the pigment and/or the filler were dispersed in the fatty phase.

Moreover, to manufacture traditional lipsticks containing waxes, the following procedure was adopted:

in a first step, a paste consisting of at least one fatty constituent and of at least one wax, the said paste optionally containing pigments and/or fillers and/or other additives, was heated to a temperature above the highest melting point of the waxes, termed finishing temperature, in a second step, the paste heated to the finishing temperature is poured into a mould, which is equivalent to a first quenching, and the mould is then cooled, constituting a second quenching.

In this process, the two successive quenchings enable the wax(es) to form a crystalline network, and consequently enable a solid product to be obtained.

According to the present invention, it was found to be possible to obtain soft pastes having a high wax content by kneading the paste during the cooling, that is to say the paste is kneaded during at least a part of the cooling in order to create zones of crushing of the paste in the bulk. It should be noted that a suitable soft paste cannot be obtained by simple stirring with shearing using a stirrer.

Consequently, the subject of the present invention is also a process for the manufacture of a composition as defined above, in which a mixture of 12–60% by weight of at least one wax having a melting point above 55° C. and at least one component taken from the group composed of fatty constituents, pigments, fillers and additives is prepared and then cooled, characterized in that the said mixture is subjected to a kneading for at least a part of the cooling.

It appears that, under these conditions, the wax crystallizes in the form of fine crystals, which would explain the fact that the composition remains in the form of a soft paste. This hypothesis must not, however, be considered in any way to limit the invention.

To perform the kneading, it is possible, in particular, to use two types of apparatus: a roll mill containing two counter-rotating rolls between which the paste passes, and a screw extruder-mixer. It is preferable to use an extruder-mixer, since a paste of very consistent quality is obtained reproducibly. Furthermore, it is possible, by adapting the exit die of the extruder-mixer, to package the composition in line at the exit of the said extruder-mixer.

According to the invention, it is preferable to use a cooker-extruder-mixer containing, in an outer barrel equipped on the exit side with an extrusion die, one (or two) shaft(s) driven in rotation so that the peripheral structure of one shaft cooperates with the outer barrel and, where appropriate, with the peripheral structure of the other shaft to effect the mixing and kneading of the paste and its movement along the barrel towards the extrusion die.

Preferably, the shaft (or each of the shafts) consists of at least two successive sleeves, the inside portion of which fits over a spindle driven in rotation, and the outside portion of which can have diverse peripheral structures; among traditional structures, there may be mentioned, on the one hand helical screw flights whose pitch conveys the processed material from the input side to the exit side of the mixer (hereinafter designated "DF"), on the other hand helical screw flights having a pitch which is the reverse of the above (hereinafter designated "CF", with a negative pitch value) which force the processed material back in the direction from the exit side to the input side of the mixer, such flights possessing longitudinal channels to effect the passage of the material towards the exit of the mixer, and lastly a multi-lobed section possessing, over its entire length, blades (or lobes) arranged side by side and angularly offset with respect to one another. A bilobate section, which possesses a succession of lobes offset by 90° with respect to one another, is designated hereinafter "BL". It is possible to have a large enough number of sleeves with external flights to vary the pitch, the depth and the number of flights in the different successive longitudinal zones of the mixer. Furthermore, the different longitudinal zones of the mixer may be heated by one or more bands arranged on the outside of the outer barrel. The heating may be performed in each band using at least one electrical resistance element or at least one heat exchanger.

According to the invention, the shaft (or each shaft) of the cooker-extruder-mixer used preferably possesses at least one "DF" sleeve forming a transport screw situated on the feed (or input) side of the mixer, at least one "CF" sleeve (termed "counterflight type") and/or one multilobe "BL" sleeve having a kneading and/or homogenizing action, and at least one "DF" sleeve forming a transport screw situated at the exit end of the mixer.

According to a first embodiment, the invention relates to a process of the type defined above, characterized in that in a first step, the mixing of all the constituents of the composition is carried out at a temperature at which the wax(es) is/are molten, and, in a second step, the hot mixture obtained is introduced into a roll mill or into a screw extruder-mixer.

According to another embodiment, the process according to the invention is characterized in that a mixture of the non-pulverulent constituents of the composition is introduced at the head of a screw extruder-mixer at a temperature at which the wax(es) is/are molten, and the pulverulent constituents of the composition are introduced into the said screw extruder-mixer at one or more-points before the extrusion die.

Several examples of implementation according to the invention will be described below, purely by way of illustration and without implied limitation.

The preparation of the compositions according to the invention defined in Examples 1 to 3 below is performed in a twin-screw cooker-extruder-mixer (type "BC 21" of the company "CLEXTRAL"), the structure of which is outlined below:

| Input ---> | | | | | | | | | | | ---> Exit |
|---|---|---|---|---|---|---|---|---|---|---|---|
| Screw structure | DF | DF | DF | DF | BL | DF | DF | CF | DF | DF | BL | DF |
| Sleeve length (mm) | 50 | 50 | 50 | 50 | 50 | 100 | 50 | 25 | 50 | 50 | 50 | 25 |
| Screw pitch length (mm) | 16.6 | 16.6 | 16.6 | 16.6 | | 25 | 16.6 | −16.6 | 16.6 | 16.6 | | 16.6 |

In the attached drawing:

FIGS. 1, 3 and 5 show in elevation sections of different types of sleeves used on the shafts of the mixer employed;

FIGS. 2, 4 and 6 show, respectively, transverse sections along II—II, IV—IV and VI—VI of FIGS. 1, 3 and 5.

By reference to the drawing, it is seen that the outer barrel of the mixer is designated 1 and the spindles of the two parallel shafts which are arranged therein are designated 2a, 2b. Adjacent sleeves are slipped over the two spindles 2a, 2b, the two shafts being equipped with the same sleeves over the same section of the length in order to cooperate mechanically with one another during rotation.

In FIGS. 1 and 2, a section in which there are "DF" type sleeves, referenced 3a, 3b, is shown. In FIGS. 3 and 4, a section in which there are "BL" type bilobate sleeves 4a, 4b is shown. In FIGS. 5 and 6, a section in which there are "CF" type sleeves 5a, 5b, with longitudinal channels 11, is shown.

In the table given above:

DF represents a twin helical-flight screw element as illustrated in FIGS. 1 and 2;

BL represents a bilobate element as illustrated in FIGS. 3 and 4; and

CF represents a screw element having a pitch which is the reverse of DF, as illustrated in FIGS. 5 and 6, possessing longitudinal channels 11.

The different elements have an external diameter of 25 mm, an internal diameter of 14 mm; the distance between the spindles of the two shafts is 21 mm.

The two shafts rotate at a speed of 300 rpm; the exit orifices have a total cross-section of 500 $mm^2$. The output is approximately 5 kg/h.

The mixture is heated to 100° C. over the first 300 mm, and then to 30° C. over the remaining 300 mm.

EXAMPLE 1

Treatment Base for the Lips

A treatment base having the following formulation (% by weight) was prepared:

Fatty Constituents:

Liquid petrolatum . . . 22%

Lanolin oil . . . 23.6%

Isopropyl lanolate . . . 24.2%

Waxes:

Microcrystalline wax . . . 15%

Carnauba wax . . . 15%

Additives:

Di-tert-butyl-4-hydroxytoluene . . . 0.2%

This composition contains 30% by weight of waxes.

The different constituents were mixed at a temperature of 100° C., and this premix was introduced at the head of the extruder-mixer defined above.

A soft paste having a dynamic viscosity of 17 Pa.s, measured using a CONTRAVES TV rotational viscometer equipped with an "MS-r4" moving element with a frequency of 60 Hz, is obtained, which paste can be readily taken up using a brush for the dermopharmaceutical treatment of the lips.

EXAMPLE 2

Lip Rouge

A lip rouge having the following formulation (% by weight) was prepared:

Fatty constituents:

Jojoba oil . . . 12%

Castor oil . . . 7%

Isopropyl lanolate . . . 20%

Waxes:

Beeswax . . . 20%

Polyethylene wax . . . 20%

Polymers:

Polybutene . . . 8%

Additive:

Butylated hydroxytoluene . . . 0.2%

Pigments:

FD βC Yellow 6 aluminium lake (CI 15,985) . . . 1%

D βC Red 27 (CI 45,410) . . . 9%

Titanium dioxide (CI 77,891) . . . 2.8%

This composition contains 40% by weight of waxes.

The different pigments were ground in the fatty constituents (castor oil, jojoba oil and isopropyl lanolate). The additive was then added and the mixture wass heated to 100° C.

The waxes were then introduced into the preheated mixture, and the whole was introduced at the head of the extruder-mixer.

A soft paste having a dynamic viscosity of 24 Pa.s, measured using a CONTRAVES TV rotational viscometer equipped with an "MS-r4" moving element with a frequency of 60 Hz, was obtained which paste could be readily taken up using a pen-style foam applicator for making up the lips.

EXAMPLE 3

Lip Rouge

A lip rouge having the following formulation (% by weight) was prepared:

Fatty Constituents:

Jojoba oil . . .20%

Liquid petrolatum . . . 13.8%

Lanolin . . .22%

Additive:

Butylated hydroxytoluene . . . 0.2%

Fillers:

Talc . . . 8%

Nylon powder . . . 8%

Wax:

Microcrystalline wax . . . 17%

Pigments:

D βC Red 7 calcium lake (CI 15,850:1) . . . 5.8%

Black iron oxide (CI 77,499) . . . 0.2%

D βC Yellow 6 aluminium lake (CI 15,985) . . . 5%

This composition contains 17% by weight of wax.

A premix was prepared at 100° C. with the fatty constituents, the wax and the additive, and this premix was introduced via a first orifice at the extruder head. The pigments were introduced at the extruder head via a second orifice, and the fillers were introduced 100 mm upstream of the die via a third orifice.

A soft paste having a dynamic viscosity of 8 Pa.s, measured using a CONTRAVES TV rotational viscometer equipped with an "MS-r4" moving element with a frequency of 60 Hz, was obtained, which paste could be readily taken up using a pen-style foam applicator for making up the lips.

We claim:

1. A cosmetic or dermopharmaceutical composition in the form of a soft paste, which can be used for making up or treating the skin or lips, said soft paste consisting of a fatty phase containing 12% to 60% by weight, relative to the total weight of the composition, of at least one wax having a melting point above 55° C., said soft paste having a dynamic viscosity at 25° C. of between 3 and 30 Pa.s, and, optionally, at least one pulverulent or fat-soluble additive mixed with the fatty phase, said at least one additive being selected from the group consisting of a pulverulent colored pigment, a dye, a pulverulent inorganic or organic filler, a lip rouge or lip treatment formulation adjuvant, a fat-soluble polymer and a fat-soluble cosmetic or dermopharmaceutical active agent;

wherein said paste is formed by heating said at least one wax in said fatty phase above the melting point of said at least one wax, and cooling said wax while kneading during at least a part of said cooling such that said soft paste is formed.

2. The composition according to claim 1, said wax being present in an amount of from 15% to 40% by weight, relative to the total weight of the composition.

3. The composition according to claim 1 wherein said at least one wax has a melting point of between 55 to 110° C. and a needle penetration value of between 3 and 40 as measured according to French Standard NFT 004.

4. The composition according to claim 1 wherein said at least one wax is selected from the group consisting of beeswaxes, carnauba, candelilla and ouricury waxes, cork fiber waxes, sugar-cane waxes, Japan waxes, microcrystalline waxes, lignite waxes, ozokerites, polyethylene waxes and the waxes obtained by Fischer-Tropsch synthesis.

5. A cosmetic or dermopharmaceutical composition in the form of a soft paste, which can be used for making up or treating the skin or lips, said soft paste being substantially anhydrous, consisting of at least one wax in a fatty phase, containing 12% to 60% by weight, relative to the total weight of the composition, of at least one wax having a melting point above 55° C., said soft paste having a dynamic viscosity at 25° C. of between 3 and 30 Pa.s, wherein said fatty phase contains at least one fatty constituent other than a wax, said fatty constituent having a melting point below 55° C., and, optionally, at least one pulverulent or fat-soluble additive mixed with the fatty phase, said at least one additive being selected from the group consisting of a pulverulent colored pigment, a dye, a pulverulent inorganic or organic filler, a lip rouge or lip treatment formulation adjuvant, a fat-soluble polymer and a fat-soluble cosmetic or dermopharmaceutical active agent;

wherein said paste is formed by heating said at least one wax in said fatty phase above the melting point of said at least one wax, and cooling said wax while kneading during at least a part of said cooling such that said soft paste is formed.

6. The composition according to claim 5, wherein said fatty constituent is an oil selected from the group consisting of paraffin oil, liquid petrolatum, mineral oils having a boiling point of between 310 and 410° C.; perhydrosqualene; sweet almond oil, calophyllum oil, palm oil, avocado oil, jojoba oil, olive oil, castor oil, cereal-germ oils; silicone oils, purcellin oil butyl myristate, isopropyl myristate, cetyl myristate, isopropyl palmitate, butyl stearate, hexadecyl stearate, isopropyl stearate, octyl stearate, isocetyl stearate, decyl oleate, hexyl laurate, propylene glycol dicaprylate, diisopropyl adipate; oleyl alcohol, linoleyl alcohol, linolenyl alcohol, isostearyl alcohol, octyl dodecanol, isopropyl lanolate, isocetyl lanolate, actylglycerides, glycol octanoates, glycerol octanoates, glycol decanoates, glycerol decanoates, cetyl ricinoleate, isopropyl oleate and isocetyl oleate.

7. The composition according to claim 5 wherein said fatty constituent is a fat selected from the group consisting of hydrogenated castor oil, hydrogenated palm oil, hydrogenated tallow, hydrogenated coconut oil, propylene glycol myristate, myristyl myristate, cetyl alcohol, monoglycerides, diglycerides, triglycerides, sucroglycerides and lanolins.

8. The composition according to claim 5 wherein said fatty constituent represents 10 to 90% by weight of the composition.

9. The composition according to claim 1 wherein said coloring agent contains at least one colored pigment selected from the group consisting of chromium oxides, black iron oxides red iron oxides, yellow iron oxides, ultramarines, manganese pyrophosphate, ferric blue, titanium dioxide, a silver powder and an aluminum powder.

10. The composition according to claim 1 wherein said coloring agent contains at least one of a pearlescent agent and an organic dye.

11. The composition according to claim 1, wherein said coloring agent represents from 0.5 to 20% by weight relative to the total weight of the composition.

12. The composition according to claim 1 wherein said filler is selected from the group consisting of talc, micas, kaolin, zinc oxides, titanium oxides, precipitated calcium carbonate, magnesium carbonate, magnesium hydrogen carbonate, silica, titanium dioxide, glass beads, ceramic beads, metal soaps, non-expanded powders of synthetic polymers, expanded powders of synthetic polymers and powders of natural organic materials.

13. The composition according to claim 1 wherein said filler represents lip to 40% by weight relative to the total weight of the composition.

14. The cornposition according to claim 1 wherein said formulation adjuvant is an antioxidant.

15. The composition according to claim 14, wherein said antioxidant represents less than 3% by weight relative to the total weight of the composition.

16. The composition according to claim 1 wherein said cosmetic active agent or dermopharmaceutical active is selected from the group consisting of a vitamin, essential fatty acids, sphingocerils and sunscreen agents which are fat-soluble.

17. The composition according to claim 1 wherein said cosmetic active agent or dermopharmaceutical active agent represents from 0.05% to 5% by weight relative to the total weight of the composition.

18. A cosmetic or dermopharmaceutical composition in the form of a soft paste, which can be used for making up or treating the skin or lips, said soft paste consisting of a fatty phase containing 12% to 60% by weight, relative to the total weight of the composition, of at least one wax having a melting point above 55° C., said soft paste having a dynamic viscosity at 25° C. of between 3 and 30 Pa.s, wherein said fatty phase contains at least one fatty constituent other than a wax, said fatty constituent having a melting point below 55° C., and, optionally, at least one pulveruleut or fat-soluble additive mixed with the fatty phase, said at least one additive comprising a pulverulent colored pigment, a dye, a pulverulent inorganic or organic filler, a lip rouge or lip treatment formulation adjuvant, a fat-soluble polymer, or a fat-soluble cosmetic or dermopharmaceutical active agent;

wherein said paste is formed by heating said at least one wax in said fatty phase above the melting point of said at least one wax, and cooling said wax while kneading during at least a part of said cooling such that said soft paste is formed.

* * * * *